(12) United States Patent
Gardner (10) Patent No.: US 8,558,203 B1
(45) Date of Patent: Oct. 15, 2013

(54) ULTRAVIOLET WAVELENGTH-TRANSFORMING SLEEVE

(71) Applicant: William G Gardner, Glendale, AZ (US)

(72) Inventor: William G Gardner, Glendale, AZ (US)

( * ) Notice: Subject to any disclaimer, the term of this patent is extended or adjusted under 35 U.S.C. 154(b) by 0 days.

(21) Appl. No.: 13/769,381

(22) Filed: Feb. 17, 2013

Related U.S. Application Data (63) Continuation of application No. 12/854,160, filed on Aug. 10, 2010, now Pat. No. 8,378,324.

(51) Int. Cl.
  *H01J 1/62* (2006.01)
  *G01N 21/00* (2006.01)
  *A61N 5/06* (2006.01)

(52) U.S. Cl.
  USPC ........... 250/504 R; 250/503.1; 250/454.11; 250/455.11; 250/505.1; 250/365; 250/493.1; 313/485

(58) Field of Classification Search
  USPC ............... 250/504 R, 503.1, 454.11, 455.11, 250/505.1, 365, 493.1; 313/485
  See application file for complete search history.

(56) References Cited

U.S. PATENT DOCUMENTS

| | | | | |
|---|---|---|---|---|
| 4,868,397 A | * | 9/1989 | Tittel | 250/455.11 |
| 7,148,497 B2 | * | 12/2006 | Gardner | 250/503.1 |
| 7,781,751 B2 | * | 8/2010 | Gardner | 250/504 R |

* cited by examiner

*Primary Examiner* — Nikita Wells

(57) ABSTRACT

This invention provides for a removable/replaceable, wavelength-transforming sleeve/sheath to be placed around a primary UV radiation source that emits a primary UV wavelength spectral distribution; such that at least a portion of the sleeve/sheath transforms at least a portion of the primary UV wavelength spectral distribution to a different secondary wavelength spectral distribution. Additionally, the sleeve/sheath may help to prevent breakage of the primary UV radiation source and to contain the broken pieces in the event of breakage. In some embodiments, a portion of the sleeve/sheath may be coupled with a UV reflective surface to direct radiation in a preferred direction. Individual sleeves/sheaths may have various patterns of wavelength-transforming materials that emit one or more secondary wavelength spectral distributions and the sleeve/sheath may also have one or more sections that allow transmission of the primary UV wavelength spectral distribution.

20 Claims, 6 Drawing Sheets

Fig. 2A

ULTRAVIOLET WAVELENGTH-TRANSFORMING SLEEVE

CROSS-REFERENCE TO RELATED APPLICATIONS

This application is a continuation-in-part of pending U.S. utility application Ser. No. 12/854,160 Titled HANDHELD PORTABLE MULTI PURPOSE STERILIZING WAVELENGTH TRANSFORMING CONVERTER, filed Aug. 10, 2010, and is incorporated by reference in its entirety herein for all purposes.

FIELD OF THE INVENTION

The present invention relates to ultraviolet radiation (UV) emitting devices used in the fields of mineralogy; scientific research; forensics; ultraviolet sterilization of food, water, air, fluids, and surfaces; area illumination; photo-chemistry, photo-medical treatments, photo-lithotropy, artistic displays of fluorescent materials; and similarly related fields. Specifically, the present invention provides several related methods and devices whereby the wavelength spectral distribution being emitted from a primary UV radiation source may be made variable and adjustable.

The electromagnetic spectrum ranges from cosmic rays at one end to radio-waves at the other end. The ultraviolet region of the electromagnetic spectrum is situated between visible light and x-rays, with the wavelengths of the UV A being shorter and more energetic than violet visible light and the wavelengths of vacuum UV being slightly longer and less energetic than x-rays. The full ultraviolet spectrum ranges from wavelengths of about 100 nanometers (nm) to 400 nm and the ultraviolet spectrum is usually divided into 4 sections; vacuum UV (also called far or very UV, from 100 nm to about 200 nm), UV C (also called germicide or short-wave UV, from 200 to about 280 nm), UV B (also called mid-wave or medium-wave UV, from 280 nm to about 320 nm), and UV A (also called poster lamp, blacklight, or long-wave UV, from 320 nm to 400 nm).

Vacuum UV reacts with oxygen to produce ozone and free oxygen, both of which are very strong oxidizing agents and which can cause chemical reactions at relatively low temperatures in a process called cold combustion. Air that is contaminated with various odiferous chemicals will be sanitized and rendered odorless via such cold combustion chemical reactions, as a result of the vacuum UV passing through the odiferous/chemically contaminated air and generating the strong oxidizing agents. UV C radiation by itself is used extensively for sterilization, purifying, and deodorizing applications in food, air, water, and general surface sterilization processes because the UV C not only deactivates microorganisms such as: bacteria, molds, spores, fungi, and viruses (by direct irradiation which damages the DNA such that the micro-organisms cannot reproduce), but the UV C radiation also breaks down the chemical bonds of alcohols, pesticides, chloramines, and other contaminants such as NDMA or MTBE. The process whereby UV radiation breaks chemical bonds is called photolysis. UV B is the agent that causes human skin to "sun-burn" and the UV B is needed to start the sun tanning process. The lamps in sun tanning booths usually emit a combination of UV B and UV A. UV B is also used extensively in various medical treatments—especially for skin diseases.

The primary wavelength spectral distribution of ultraviolet radiation can be emitted from a variety of sources including but not limited to: light emitting diodes (LED's), UV lasers, electric arcs (especially as in arc welding), xenon bulbs, halogen bulbs, excimer bulbs, and mercury vapor lamps/tubes of low, medium and high pressures.

Now with respect to certain high energy light sources such as mercury vapor discharge bulbs, it is well known that the phosphors coated on the interior wall of a mercury vapor discharge bulb suffer from exposure to the electric current, mercury atoms and ions, and short-wave ultraviolet light particularly of wavelengths less than 200 nm, for instance, the 185 nm far UV emission of mercury vapor. The present invention solves the problem of degradation of phosphors and other wavelength-transforming materials, by coupling wavelength-transforming materials with a sleeve/sheath, external to the lamp environment, thereby removing the wavelength-transforming materials from the harsh environment existing inside the primary UV radiation sources.

SUMMARY OF THE INVENTION

One object of the present invention is to provide a removable/replaceable, wavelength-transforming sleeve/sheath that is positioned externally to the outside envelope of the primary UV radiation source, where at least a portion of the sleeve/sheath has wavelength-transforming properties such that in response to illumination by a primary UV radiation source, the sleeve/sheath will selectively transform at least a portion of the primary UV wavelength spectral distribution to a secondary wavelength spectral distribution that is different from the emission of the primary UV radiation source.

Another object of the present invention is to provide a re-usable removable/replaceable sleeve/sheath thus preventing the phosphors or other wavelength-transforming materials from being discarded, thus making the sleeve/sheath environmentally friendly and allowing the sleeve/sheath materials to easily be sorted from the other components such as the glass envelope, the mercury, and the other metallic components of the primary UV radiation source.

A further object of the invention is to greatly extend the useful lifetime of the phosphor, or other wavelength-transforming material, by removing it from the harsh environment that exists inside a lamp envelope and relocating the wavelength-transforming material to a sleeve/sheath external to the envelope of the primary UV radiation source.

Yet another object of the invention is to provide a sleeve/sheath that covers only a portion of the primary UV radiation source thereby providing a combination of both primary and transformed wavelength spectral distributions.

Another object of the invention is to provide a wavelength-transforming sleeve/sheath that serves as a shield to protect the primary UV radiation source from breakage and also to contain the broken pieces (such as mercury or glass) if such breakage of the primary UV radiation source should occur.

A further object of the invention is that a portion of the sleeve/sheath may be coupled with a substance to reflect UV to direct and concentrate the various emissions in a preferred radial area.

Another object of the invention is to provide various patterns of wavelength-transforming material to cause the emission wavelength to vary according to the selected pattern.

DETAILED DESCRIPTION OF THE INVENTION

For the purposes of this invention, the primary UV radiation source may be selected from any of the known UV sources such as: light emitting diodes (LED's), lasers, electric arcs, xenon lamps/bulbs, excimer lamps/bulbs, and mercury vapor tubes/lamps of low, medium and high pressures.

Although the wavelength-transforming materials used in similar applications are typically phosphors, any of a wide variety of other wavelength-transforming materials may be used in this invention without departing from the teaching. Further, the wavelength-transforming materials may have structural properties such that the material is self supporting, or the wavelength-transforming materials may need to be supported by a structural member—i.e. the sleeve/sheath. As described in the incorporated references, if support is needed, the wavelength-transforming materials may be coupled to either side of a UV transmitting support surface, bonded between UV transmitting support surfaces, sandwiched between two layers of UV transmitting materials, or the wavelength-transforming material may be disposed internally to the UV transmitting support material. Further, the wavelength-transforming material may be constructed of a mat of fibers (similar to fiber-glass matting) or the material may be woven into a screen (similar to fiber-glass cloth). It should be noted that many materials other than phosphors have wavelength-transforming properties. For example, borosilicate glass will block the UV that produces ozone.

If the sleeve/sheath is to be hard and rigid, the material comprising the sleeve/sheath can be chosen from the group of materials that includes natural or synthetic fused quartz or quartz glass, borosilicate glass, natural or synthetic calcium fluoride (also the other metallic fluorides such as barium, lithium, sodium, magnesium, strontium, and lanthanum fluoride), natural or synthetic sapphire, magnesium oxide, hard glass, lime glass, chemical Pyrex, sapphire glass, or UV transmitting or UV minimizing Plexiglass. If the sleeve/sheath is to be flexible, the material comprising the sleeve/sheath can be chosen from the group of materials that include silicone polymers or fluoropolymers. One such group of fluoropolymers is the Teflon® family which have acronyms such as ETFE, Tefzel®, PFA, PTFE, FEP and EFEP.

The present invention is particularly suitable for simplifying the manufacturing process of various fluorescent tubes/lamps. Such mercury vapor discharge lamps are widely available in a variety of sizes and configurations, and are known to provide reliable and effective operation. Currently, a fluorescent lamp/tube manufacturer produces dozens of tubes/lamps each having the same dimensions and power requirements, often with the only difference being the kind of phosphor that coats the inside of the fluorescent tube/lamp or the kind of glass that is used for the outside envelope. Therefore, the manufacturer, the distributors, and the companies that manufacture items containing such various tubes/lamps, all need to stock a supply of each of the various kinds of tube/lamp. With the ability to have the phosphor or other wavelength-transforming material associated with (or coupled with) a protective sleeve/sheath, the variety of tubes/lamps to be manufactured or kept in stock can be minimized as can the space required to store them. For example, instead of stocking 100 UV C tubes, 100 UV B tubes, 100 UV A tubes, and 100 white light tubes, a company could more easily stock 200 UV C tubes/lamps and a selection of sleeves to convert them to the desired wavelength. Further, in the event that the filaments were to burn out in a particular tube/lamp, the wavelength-transforming sleeve/sheath can be removed and placed on a different tube/lamp. Further still, tube/lamp manufacturers do not make some lamps/tubes in certain sizes that emit specific wavelengths (except possibly as an expensive custom ordered item). For one example, Philips lighting currently makes the high output UV C tubes/lamps in a 35 watt version, a 60 watt version and a 95 watt version. However, Philips lighting does not make a similar high output tube/lamp in any other wavelength. In addition to the protective aspects of the sleeve/sheath, the use of a sleeve/sheath as described in this invention will allow any of the Philips high output tubes/lamps to be converted to any other wavelength or plurality of wavelengths as desired, thus providing a product that otherwise would not readily be available.

Figure 1A:
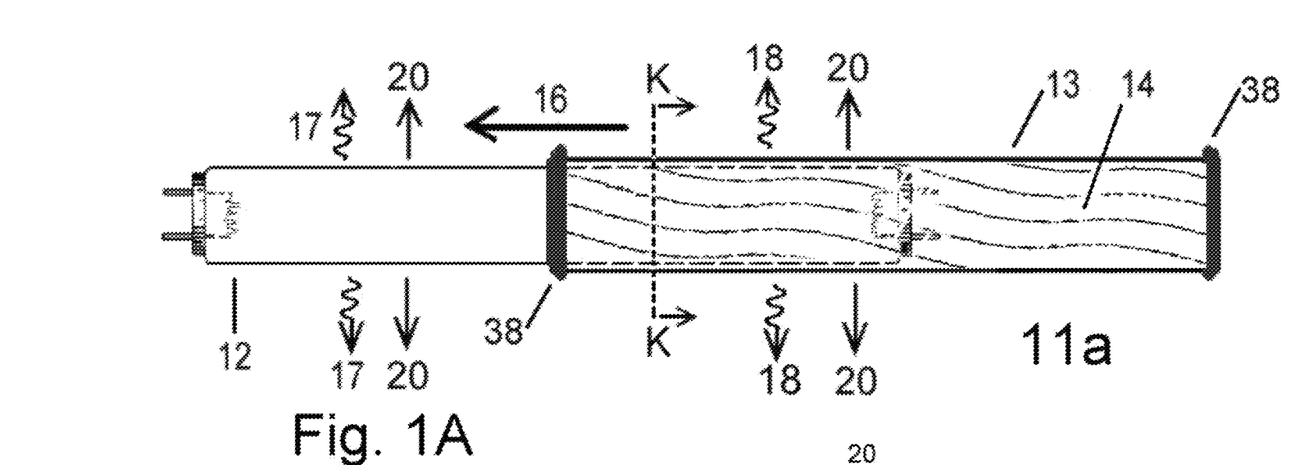
FIG. 1A is a plan view of a first embodiment showing apparatus 11a, a removable/replaceable, wavelength-transforming sleeve/sheath with a distribution of wavelength-transforming materials and a cylindrical, tubular shaped primary UV radiation source.
Figure 1B:
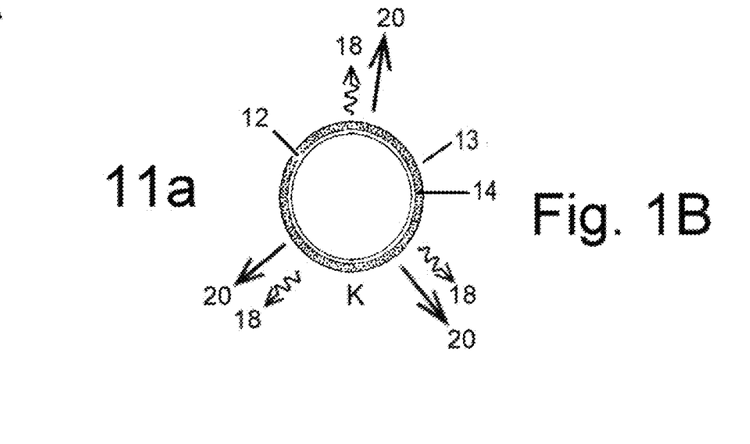
FIG. 1B is a cross-sectional view of apparatus 11a taken on the line K - - - K, depicting the removable/replaceable, wavelength-transforming sleeve/sheath positioned around the primary UV radiation source.

Referring now to FIG. 1A and FIG. 1B, the apparatus 11a shows a first embodiment with a primary UV radiation source 12 and a sleeve/sheath 13; wherein the primary UV radiation source 12 is a low pressure mercury vapor tube of cylindrical shape and the sleeve/sheath 13 is the proper shape and size to fit closely about the primary UV radiation source 12; and wherein the sleeve/sheath 13 itself may be made of a wavelength-transforming material 14, or as previously described, the wavelength-transforming material 14, such as a phosphor or other material having wavelength transforming properties, may be coupled either on the inner surface of the sleeve/sheath 13, the outer surface of the sleeve/sheath 13, inherently within the material of the sleeve/sheath 13, or sandwiched between two layers making the sleeve/sheath 13 a laminate. Further, the sleeve/sheath 13, may be constructed as a solid, or it may be a more porous construction as in a mat of fibers or a woven screen or cloth. The sleeve/sheath 13 is coaxially placed in relatively close proximity (or even contiguous) to the outside envelope of the primary UV radiation source 12. To change the emission spectra from one wavelength band to another band, the sleeve/sheath 13 (having a particular wavelength-transforming material 14) has to be removed and replaced with a different sleeve/sheath 13 (having a different wavelength-transforming material 14). Arrows show the primary UV radiation emission 17. Arrows show the transformed radiation emission 18. Arrows also indicate the preferred direction of emission 20. The selection method to determine the selected transformed radiation emission 18 wavelength of the apparatus 11a, is to first determine the desired wavelength of the transformed radiation emission, couple the appropriate wavelength transforming materials (14a, b, c, ... n—not shown herein) into a sleeve/sheath, and then slide the resultant sleeve/sheath (13a, b, c, ... n—not shown herein) over the primary UV radiation source 12. This method enables having multiple sleeve/sheaths 13 at hand such that the user can quickly and easily slide them over the primary UV radiation source 12 in the direction of arrow 16. In addition to providing a support structure for the wavelength-transforming material 14, the sleeve/sheath 13, also acts as a protective barrier to shield the primary UV radiation source 12 from harm and extremes of temperature. Additionally, if the primary UV radiation source 12 were to be broken, the sleeve/sheath 13 would contain any parts or pieces—particularly any broken glass or mercury that may be present. To assist with the containment process, the sleeve/sheath 13 may be coupled to the primary UV radiation source 12 by a coupling ring 38. Line K - - - K represents the plane for cross-sectional view K.

FIG. 1B is a cross-sectional view at line K - - - K, of apparatus 11a showing the primary UV radiation source 12 is inside the sleeve/sheath 13 which may be coupled with a wavelength-transforming material 14 as previously described. Arrows show the transformed radiation emission 18 and arrows also show the preferred direction of emission 20 which is radially outward and perpendicular to the surface of the primary UV radiation source 12 and therefore also radially perpendicular to the surface of the sleeve/sheath 13.

Figure 1C:
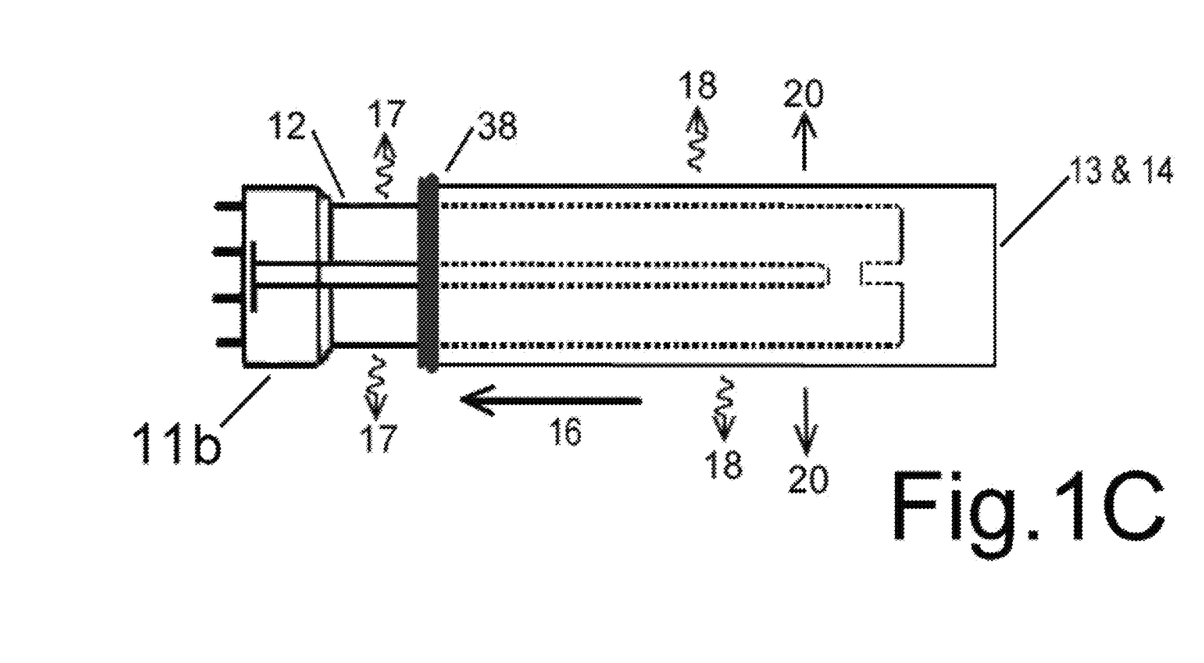
FIG. 1C is a plan view of an alternate shape of the first embodiment showing apparatus 11b, a removable/replaceable, wavelength-transforming sleeve/sheath positioned around a primary UV radiation source that is an "H" shaped tube/lamp.

FIG. 1C is a plan view of apparatus 11b showing that the primary UV radiation source 12 is a low pressure mercury vapor lamp/tube of a different shape, commonly referred to as an "H" tube wherein the primary UV radiation source 12 is coaxially surrounded by a sleeve/sheath 13. As in the previous figures, the sleeve/sheath 13 itself may be made of a wavelength-transforming material 14, or wavelength-transforming material 14 (such as a phosphor) may be coupled with the sleeve/sheath 13, as previously described. In this alternate means of the embodiment, the sleeve/sheath 13 is roughly oval in cross section and closed at one end, such that the sleeve/sheath 13 fits closely about the "H" tube primary UV radiation source 12. As has been previously described, the sleeve/sheath 13 serves as a protective barrier for the primary UV radiation source 12 and the sleeve/sheath is coupled to the primary UV radiation source 12 via coupling ring 38 to assist the sleeve/sheath 13 in containing any pieces if the primary UV radiation source 12 were to break. Additionally, as previously described, the selection method to determine the selected transformed radiation emission 18 wavelength of the apparatus 11b, is to first determine the desired wavelength of the transformed radiation emission, couple the appropriate wavelength transforming materials (14a, b, c, ... n—not shown herein) into a sleeve/sheath, and then slide the resultant sleeve/sheath (13a, b, c, ... n—not shown herein) over the primary UV radiation source 12. This method enables having multiple sleeve/sheaths 13 at hand such that the user can quickly and easily slide them over the primary UV radiation source 12 in the direction of arrow 16. To select a different transformed wavelength emission 18n (not shown herein), a different sleeve/sheath 13 is placed around the primary UV radiation source 12. Arrows represent the primary UV radiation emission 17 and arrows represent the transformed radiation emission 18. Arrows represent the general preferred direction of emission 20, which is radially outward and perpendicular to the surface of the sleeve/sheath 13 except at the closed end.

Figure 2A:
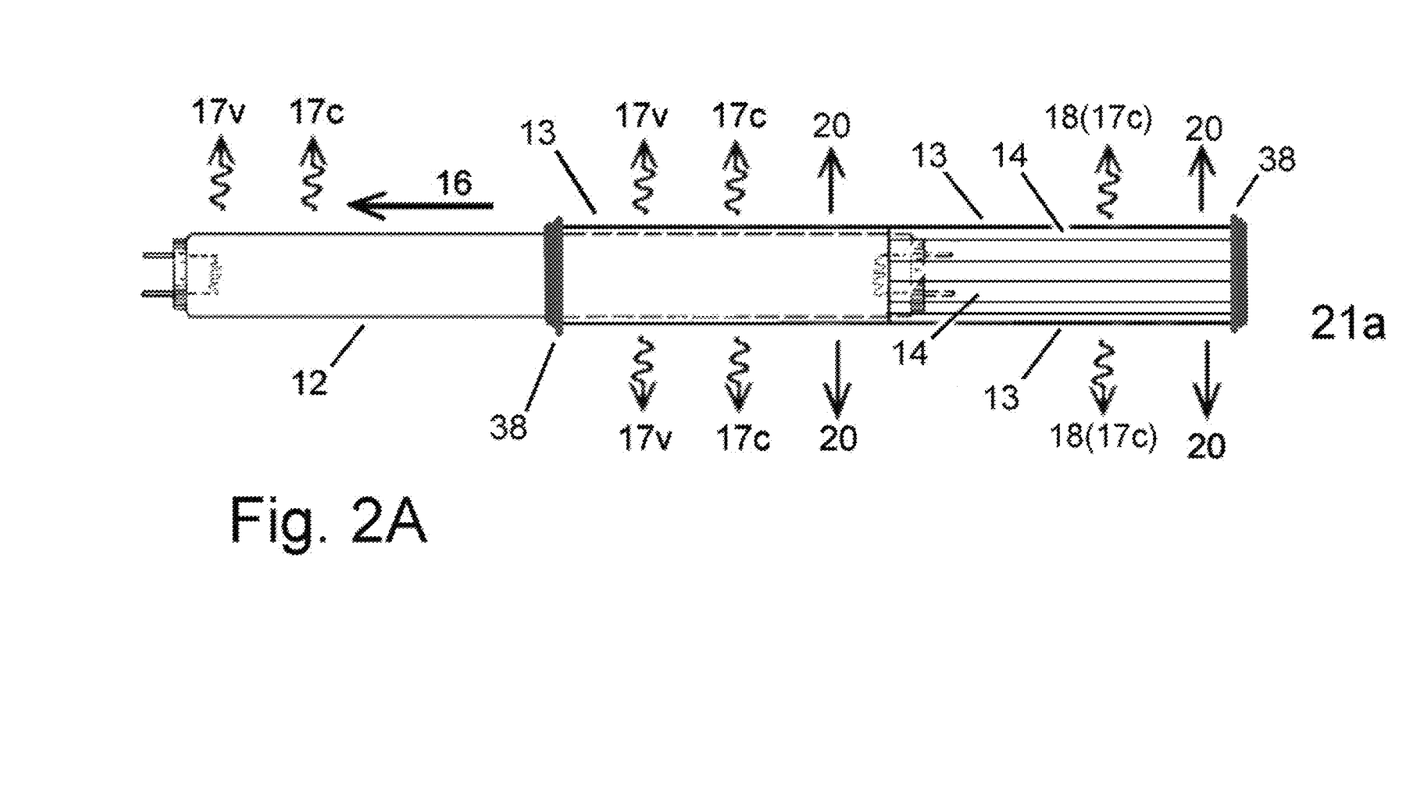
FIG. 2A is a plan view of a second embodiment showing apparatus 21a, a primary UV radiation source and a removable/replaceable, wavelength-transforming sleeve/sheath wherein a portion of the sleeve/sheath has wavelength-transforming materials arranged in a first pattern at one end of the sleeve/sheath and a second portion at the opposite end of the sleeve/sheath lacking wavelength-transforming materials.
Figure 2B:
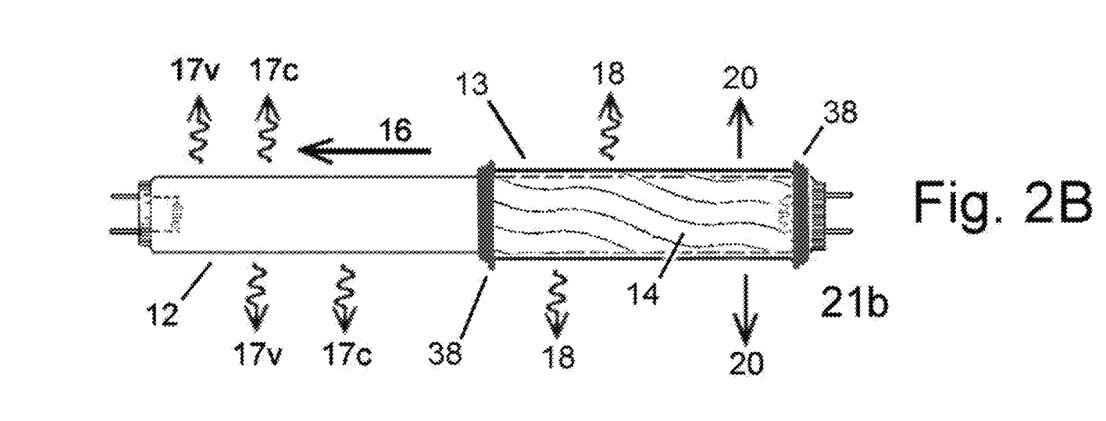
FIG. 2B is a plan view of the second embodiment showing apparatus 21b, a partial sleeve/sheath covering only a portion of a primary UV radiation source, wherein the partial sleeve/sheath has wavelength-transforming materials.
Figure 2C:
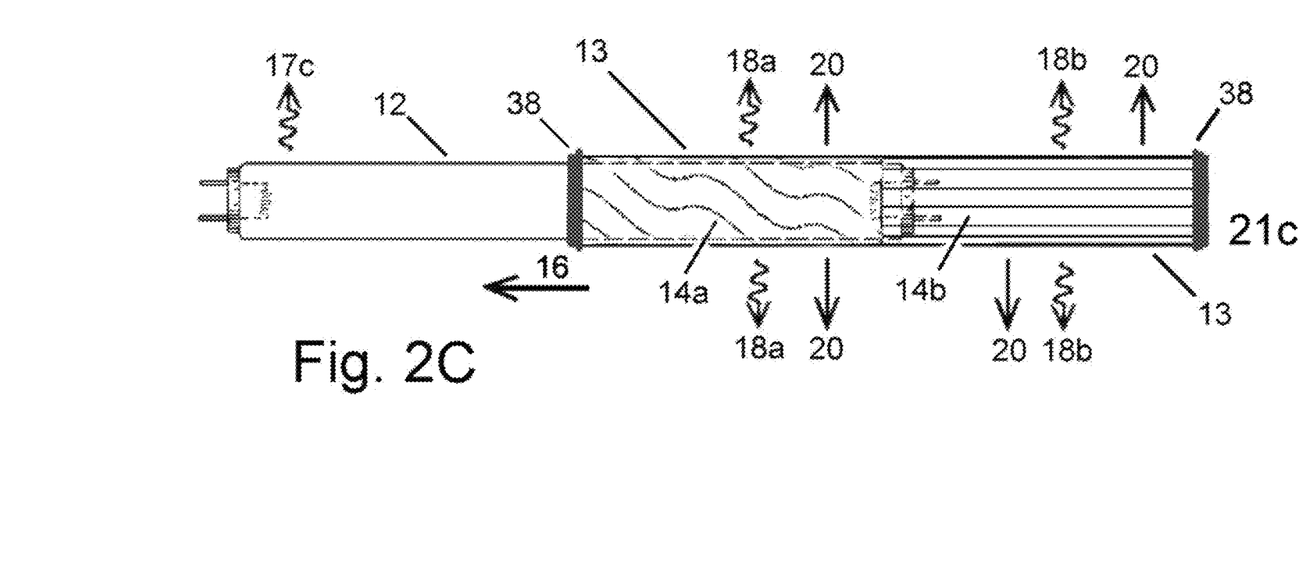
FIG. 2C is a plan view of the second embodiment showing apparatus 21c, a primary UV radiation source and a sleeve/sheath, wherein the sleeve/sheath has wavelength-transforming materials arranged in a plurality of patterns coupled to the sleeve/sheath.
Figure 3A:
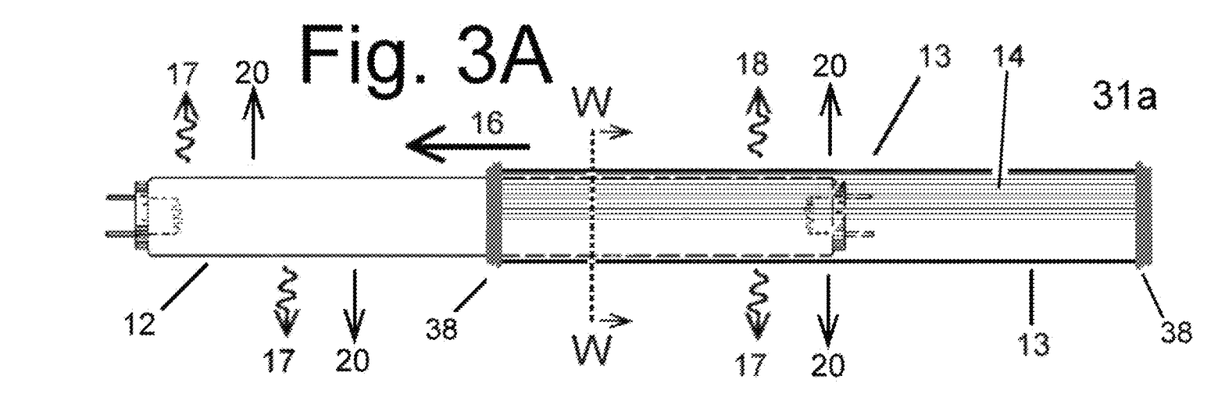
FIG. 3A is a plan view of a third embodiment showing apparatus 31a, a primary UV radiation source and a sleeve/sheath, wherein a portion of the sleeve/sheath has wavelength-transforming materials arranged in a pattern having two longitudinal stripes such that one radial side of the sleeve/sheath emits lacks any wavelength-transforming material such that an un-transformed primary wavelength spectral distribution will pass through, and the other radial side having wavelength-transforming material coupled to the sleeve/sheath.
Figure 3B:
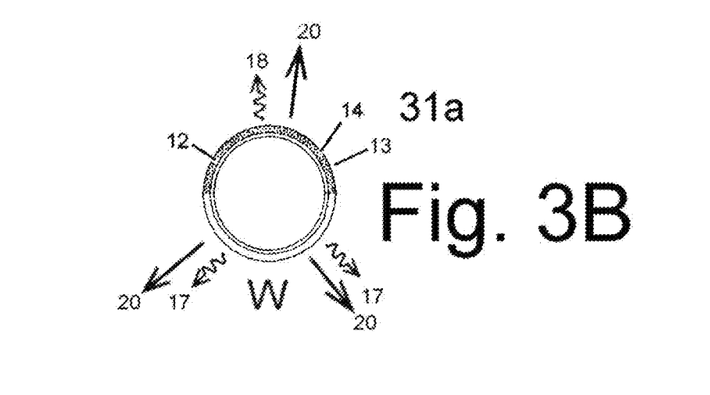
FIG. 3B is a cross-sectional view of apparatus 31a taken on the line W - - - W.
Figure 3C:
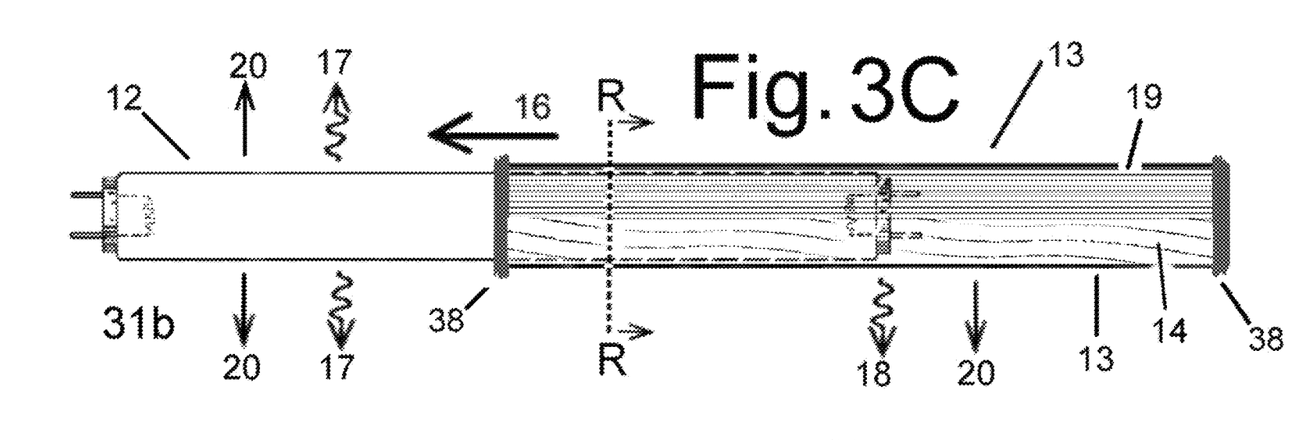
FIG. 3C is a plan view of the third embodiment showing apparatus 31b, a primary UV radiation source and a sleeve/sheath, wherein a portion of the sleeve/sheath has wavelength-transforming materials arranged in a pattern with two longitudinal stripes wherein one longitudinal side of the sleeve/sheath has reflective material coupled to the sleeve/sheath and the other longitudinal side is coupled with wavelength-transforming material.
Figure 3D:
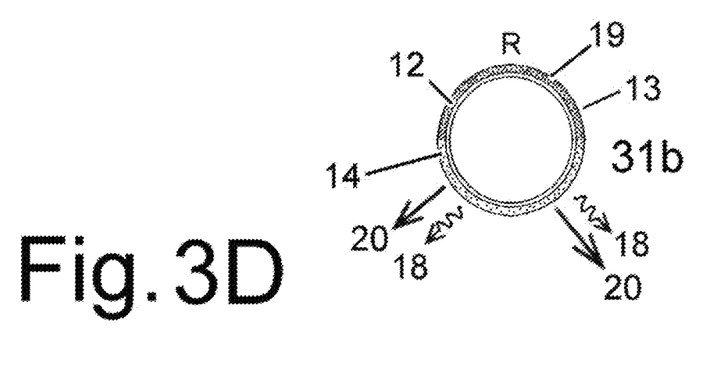
FIG. 3D is a cross-sectional view of apparatus 31b taken on the line R - - - R.

In yet further embodiments, as shown by FIGS. 2A, 2B, 2C, 3A, 3B, 3C, the wavelength-transforming material 14 is distributed in patterns that can range from simple to fairly complex. Even simple patterns of wavelength-transforming materials 14 will allow some unusual functions to be performed with a single primary UV radiation source 12. For example, three simple patterns that produce vastly different effects are: a first pattern as shown in FIGS. 2A, 2B, 2C wherein a plurality of wavelength spectral distributions are emitted longitudinally; a second pattern as shown by FIGS. 3A & 3B wherein a plurality of wavelength spectral distributions are emitted radially; a third pattern as shown by FIGS. 3C & 3D wherein wavelength spectral distributions are concentrated and emitted in a radial band. It should be noted that these patterns are examples only and that many more patterns are possible without departing from the principles of this invention.

Referring now specifically to FIG. 2A, in apparatus 21a, the wavelength-transforming material 14, is arranged in a first pattern such that the sleeve/sheath 13 is divided into two lateral portions with each portion being 100% of the circumference and each portion extending for a part of the length of the sleeve/sheath 13. In this embodiment, the primary UV radiation source 12 is an ozone producing low pressure mercury vapor tube/lamp, that emits wavelength spectral distributions primarily comprising both vacuum UV 17v and germicidal UV C 17c simultaneously. Arrows show the two primary UV emission wavelengths—vacuum UV 17v and germicidal UV C 17c respectively. The sleeve/sheath 13 is coupled with the wavelength-transforming material 14 arranged such that, once in place upon the primary UV radiation source 12, one end of the sleeve/sheath 13 allows the primary UV radiation wavelength spectral distributions of the vacuum UV 17v and germicidal UV C 17c to be transmitted and the other end only allows the UV C 17c to be transmitted through the sleeve/sheath. It should be noted that the process of filtering the UV 17v is the process of wavelength transformation as the original spectral distribution comprised both vacuum UV 17v and germicidal UV C 17c and the wavelength-transforming material 14, coupled to the sleeve/sheath 13 transforms the spectral distribution to a secondary transformed radiation emission 18, which in the present embodiment is UV C 17c. Accordingly, one end of the assembly 21a will emit both vacuum UV 17v and germicidal UV C 17c while the other end of the assembly 21a will emit only germicidal UV C 17c wavelength spectral distribution, which is the transformed radiation emission 18. Additionally, as previously described, the selection method to determine the selected transformed radiation emission 17n (not shown herein) wavelength of the apparatus 21a, is to first determine the desired wavelength of the transformed radiation emission, couple the appropriate wavelength transforming materials (14a, b, c, . . . n not shown herein) into a sleeve/sheath, and then slide the resultant sleeve/sheath (13a, b, c, . . . n—not shown herein) over the primary UV radiation source 12. This method enables having multiple sleeve/sheaths 13 at hand such that the user can quickly and easily slide them over the primary UV radiation source 12 in the direction of arrow 16. The sleeve/sheath 13 can also be coupled to the primary UV radiation source 12 with coupling rings 38 at each end. Arrows indicate the preferred directions of emission 20 which is radially outward and perpendicular to the surface of the sleeve/sheath 13.

Ultraviolet radiation in wavelengths shorter than approximately 240 nm, vacuum UV 17v, interacts with oxygen molecules in air ($o_2$) to produce ozone ($o_3$) and atomic oxygen (O). Neither the atomic oxygen nor the ozone is stable. Ozone has a half-life measured in hours and, in addition to the natural half-life decay, longer wavelengths of UV (above approximately 240 nm) such as 254 nm germicidal UV 17c react with the ozone ($o_3$) and also with the atomic oxygen (O) to break the ozone molecules apart and/or to recombine the atomic oxygen back into oxygen molecules ($o_2$). Both atomic oxygen and ozone are strong oxidizing agents that will kill microorganisms such as viruses, molds, spores, germs and bacteria. Both ozone and atomic oxygen neutralize harmful, and/or odor causing hydrocarbons, alcohols, and pyrogens (reactive molecules) by oxidizing them as if they were being burned, i.e. converted to carbon dioxide. Ozone can have negative health effects on people and other mammals, therefore the Food and Drug Administration (FDA) has set ozone exposure limits for time and concentration amounts in human occupied areas. A particular use of this embodiment is that one end of the apparatus 21a produces ozone to cleanse and sanitize proximate air and thus neutralize any odors, while the UV C 17c emitted at the other end of the apparatus 21a eliminates any excess ozone by recombining the ozone and the free oxygen.

Referring now specifically to FIG. 2b, in apparatus 21b, the sleeve/sheath 13 is a shortened cylinder that only covers a portion of the primary UV radiation source 12. Although the embodiment depicts approximately half of the primary UV radiation source 12 being surrounded, more or less of the primary UV radiation source 12 may be covered by extending or shortening the length of the sleeve/sheath 13. In this embodiment, the primary UV radiation source 12 is an ozone producing low pressure mercury vapor tube/lamp, that emits wavelength spectral distributions primarily comprising both vacuum UV 17v and germicidal UV C 17c simultaneously. Arrows show the two primary UV emission wavelengths—vacuum UV 17v and germicidal UV C 17c respectively. The sleeve/sheath 13 is coupled with the wavelength-transforming material 14 arranged such that, once in place upon the primary UV radiation source 12, uncovered portion of the sleeve/sheath 13 allows the primary UV radiation wavelength spectral distributions of the vacuum UV 17v and germicidal UV C 17c to be transmitted unimpeded, and the other end only allows the UV C 17c, as transformed radiation emission 18, to be transmitted through the sleeve/sheath. It should be noted that the process of filtering the UV 17v is the process of wavelength transformation as the original spectral distribution comprised both vacuum UV 17v and germicidal UV C 17c and the wavelength-transforming material 14, coupled to the sleeve/sheath 13 transforms the spectral distribution to a secondary transformed radiation emission 18, which in the present embodiment is UV C 17c. Accordingly, one end of the assembly 21a will emit both vacuum UV 17v and germicidal UV C 17c while the other end of the assembly 21a will emit only germicidal UV C 17c wavelength spectral distribution, which is the transformed radiation emission 18. Additionally, as previously described, the selection method to determine the selected transformed radiation emission 17n (not shown herein) wavelength of the apparatus 21b, is to first determine the desired wavelength of the transformed radiation emission, couple the appropriate wavelength transforming materials (14a, b, c, . . . n not shown herein) into a sleeve/sheath, and then slide the resultant sleeve/sheath (13a, b, c, . . . n—not shown herein) over the primary UV radiation source 12. This method enables having multiple sleeve/sheaths 13 at hand such that the user can quickly and easily slide them over the primary UV radiation source 12 in the direction of arrow 16. The sleeve/sheath 13 can also be coupled to the primary UV radiation source 12 with coupling rings 38 at each end. Arrows indicate the preferred directions of emission 20 which is radially outward and perpendicular to the surface of the sleeve/sheath 13.

Referring now specifically to FIG. 2C, apparatus 21c shows the primary radiation source 12 is a UV C producing tube/lamp. The arrows as indicated by 17c show that the primary radiation source 12 emits a primary wavelength spectral distribution of UV C radiation 17c. The sleeve/sheath 13 is coupled with two wavelength-transforming materials 14a and 14b arranged in the first pattern such that one end of the sleeve/sheath 13 transforms the primary radiation UV C radiation 17c into UV A 18a and the other end transforms the primary radiation UV C radiation 17c into UV B 18b. Additionally, as previously described, the selection method to determine the selected transformed radiation emission 18n wavelength of the apparatus 21b, is to first determine the desired wavelength of the transformed radiation emission, couple the appropriate wavelength transforming materials (14a, b, c, . . . n not shown herein) into a sleeve/sheath, and then slide the resultant sleeve/sheath (13a, b, c, . . . n—not shown herein) over the primary UV radiation source 12. This method enables having multiple sleeve/sheaths 13 at hand such that the user can quickly and easily slide them over the primary UV radiation source 12 in the direction of arrow 16. The sleeve/sheath 13 can also be coupled to the primary UV radiation source 12 with coupling rings 38 at each end. Arrows 20 indicate the preferred directions of emission which are radially outward and perpendicular to the surface of the sleeve/sheath 13.

Referring now specifically to FIGS. 3A & 3B, a different pattern of wavelength-transforming materials is shown by both the plan view in FIG. 3A and the cross-sectional view in FIG. 3B. Apparatus 31a is shown such that the sleeve/sheath 13 is coupled with wavelength-transforming material 14 arranged in a pattern to uniformly cover only one longitudinal side of the sleeve/sheath 13 (although 50% of the circumference of the sleeve/sheath 13 extending for the whole length of the sleeve/sheath 13 is depicted, lesser or greater percentages of the radial may be utilized without departing from the teaching of the present invention), with the remaining longitudinal side not having wavelength-transforming material 14 (although 50% of the circumference of the sleeve/sheath 13 extending for the whole length of the sleeve/sheath 13 is depicted, lesser or greater percentages of the radial may be utilized without departing from the teaching of the present invention) thus allowing the primary radiation to be emitted from one longitudinal side of the sleeve/sheath 13 and transformed radiation emission 18 to be emitted from the other longitudinal side of the sleeve/sheath 13. Additionally, as previously described, the selection method to determine the selected transformed radiation emission 18 wavelength of the apparatus 11b, is to first determine the desired wavelength of the transformed radiation emission, couple the appropriate wavelength transforming materials (14a, b, c, ... n not shown herein) into a sleeve/sheath, and then slide the resultant sleeve/sheath (13a, b, c, ... n—not shown herein) over the primary UV radiation source 12. This method enables having multiple sleeve/sheaths 13 at hand such that the user can quickly and easily slide them over the primary UV radiation source 12 in the direction of arrow 16. The sleeve/sheath 13 can also be coupled to the primary UV source 12 with coupling rings 38 at each end. Arrows 20 indicate the preferred directions of emission which are radially outward and perpendicular to the surface of the sleeve/sheath 13. In sum, this embodiment allows a plurality of transformed wavelength spectral distributions to be selected and emitted in a variable and infinite number of combinations. Line W - - - W shows the plane of the cross-sectional view as shown in FIG. 3B.

Referring now specifically to FIGS. 3C & 3D, an additional pattern as shown by both the plan view in FIG. 3C and the cross-sectional view in FIG. 3D is presented. Apparatus 31b has a sleeve/sheath 13 coupled with two longitudinal stripes, whereby the wavelength-transforming material 14 is arranged in a pattern to uniformly cover one full-length longitudinal side of the sleeve/sheath 13 (although 50% of the circumference of the sleeve/sheath 13 extending for the whole length of the sleeve/sheath 13 is depicted, lesser or greater percentages of the radial may be utilized without departing from the teaching of the present invention), with the remaining longitudinal side of the sleeve/sheath 13 coupled with a reflective material 19 (although 50% of the circumference of the sleeve/sheath 13 extending for the whole length of the sleeve/sheath 13 is depicted, lesser or greater percentages of the radial may be utilized without departing from the teaching of the present invention) thus forcing all of the transformed radiation 18 to be emitted from the opposite side of the sleeve/sheath 13. In FIG. 3D, line R - - - R shows the plane of the cross-sectional view. Additionally, as previously described, the selection method to determine the selected transformed radiation emission 18 wavelength of the apparatus 31b, is to first determine the desired wavelength of the transformed radiation emission, couple the appropriate wavelength transforming materials (14a, b, c, ... n not shown herein) into a sleeve/sheath, and then slide the resultant sleeve/sheath (13a, b, c, ... n—not shown herein) over the primary UV radiation source 12. This method enables having multiple sleeve/sheaths 13 at hand such that the user can quickly and easily slide them over the primary UV radiation source 12 in the direction of arrow 16. The sleeve/sheath 13 can also be coupled to the primary UV source 12 with coupling rings 38 at each end. Arrows 20 indicate the preferred directions of emission which are radially outward and perpendicular to the surface of the sleeve/sheath 13 in a desired specific radial pattern as desired.

It should be noted that similar apparatuses can be made with sleeve/sheath 13 that have additional stripes and or patterns of wavelength-transforming materials 14 without departing from the principles of the invention.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow. It will doubtless be understood to those of ordinary skill in the art that there are other embodiments employing these principles that are not described in detail herein.

I claim:

1. A system of removable/replaceable UV transforming sleeves for selectably producing multiple and variable wavelength distributions of UV when placed about a UV radiation source, comprising:
   at least one sleeve/sheath;
   at least one selected specific UV band—UV transforming material coupled to at least a selected portion of said sleeve/sheath;
   wherein said UV transforming material is external to the environment of UV production; and
   wherein said sleeve/sheath is slidably inserted about and surrounding a UV source.

2. The system of claim 1 wherein said sleeve/sheath is shaped to closely conform to the envelope shape of the UV source.

3. The system of claim 2 wherein said sleeve/sheath is cylindrically shaped.

4. The system of claim 2 wherein said sleeve/sheath is oval shaped.

5. The system of claim 2 further comprising at least one gasket coupled to at least on end of said sleeve/sheath.

6. The system of claim 5 further comprising a reflective material coupled to at least a portion of said sleeve/sheath.

7. The system of claim 6 further comprising at least one additional selected specific UV band—UV transforming material coupled to at least a selected portion of said sleeve/sheath.

8. The system of claim 1 further comprising at least one additional selected specific UV band—UV transforming material coupled to at least a selected portion of said sleeve/sheath wherein said at least one additional selected specific UV band—UV transforming material is coupled to said sleeve/sheath in a pattern differing from the pattern that said at least one selected specific UV band—UV transforming material is coupled to said sleeve/sheath.

9. The system of claim 8 wherein said sleeve/sheath is shaped to closely conform to the envelope shape of the UV source.

10. The system of claim 9 further comprising a reflective material coupled to at least a portion of said sleeve/sheath.

11. A removable/replaceable UV transforming sleeve for selectably producing multiple and variable wavelength distributions of UV when placed about a UV radiation source, comprising:
    at least one sleeve/sheath;
    at least one selected specific UV band—UV transforming material coupled to at least a selected portion of said sleeve/sheath;
    wherein said UV transforming material is external to the environment of UV production; and
    wherein said sleeve/sheath is slidably inserted about and surrounding a UV source.

12. sleeve of claim 11 wherein said sleeve/sheath is shaped to closely conform to the envelope shape of the UV source.

13. The sleeve of claim 12 wherein said sleeve/sheath is cylindrically shaped.

14. The sleeve of claim 12 wherein said sleeve/sheath is oval shaped.

15. The sleeve of claim 12 further comprising at least one gasket coupled to at least on end of said sleeve/sheath.

16. The sleeve of claim 15 further comprising a reflective material coupled to at least a portion of said sleeve/sheath.

17. The sleeve of claim 16 further comprising at least one additional selected specific UV band—UV transforming material coupled to at least a selected portion of said sleeve/sheath.

18. The sleeve of claim 11 further comprising at least one additional selected specific UV band—UV transforming material coupled to at least a selected portion of said sleeve/sheath wherein said at least one additional selected specific UV band—UV transforming material is coupled to said sleeve/sheath in a pattern differing from the pattern that said at least one selected specific UV band—UV transforming material is coupled to said sleeve/sheath.

19. The sleeve of claim 18 wherein said sleeve/sheath is shaped to closely conform to the envelope shape of the UV source.

20. The sleeve of claim 19 further comprising a reflective material coupled to at least a portion of said sleeve/sheath.

\* \* \* \* \*